United States Patent [19]

Molacek et al.

[11] Patent Number: 5,375,609
[45] Date of Patent: Dec. 27, 1994

[54] PACING LEAD INSULATOR

[75] Inventors: Richard L. Molacek, Maple Grove; Kenneth E. Cobian, St. Anthony; Michael J. Ebert, Fridley; Allan H. Jevne, Anoka; James R. Keogh, Maplewood; Paul C. Slaikeu, Vadnais Heights, all of Minn.

[73] Assignee: Medtronic, Inc., Minneapolis, Minn.

[21] Appl. No.: 33,529

[22] Filed: Mar. 22, 1993

Related U.S. Application Data

[63] Continuation-in-part of Ser. No. 825,694, Jan. 27, 1992, abandoned.

[51] Int. Cl.$^5$ ............................................. A61N 1/04
[52] U.S. Cl. ................................................... 607/119
[58] Field of Search ...................... 623/1, 66; 607/122; 128/784, 785, 786, 783

[56] References Cited

U.S. PATENT DOCUMENTS

| | | |
|---|---|---|
| 4,851,009 | 7/1989 | Pinchuk . |
| 4,873,308 | 10/1989 | Coury . |
| 5,019,096 | 5/1991 | Fox, Jr. et al. ............... 623/1 |
| 5,040,544 | 8/1991 | Lessar . |
| 5,109,077 | 4/1992 | Wick . |
| 5,133,742 | 7/1992 | Pinchuk . |

OTHER PUBLICATIONS

"Cellular Interactions with Biomaterials: In Vivo Cracking of Pre-Stressed Pellethane 2363–80A", by Q. Zhao et al., Journal of Biomedical Materials Research, vol. 24, 621–637 (1990).

"In Vivo Degradation of Polymers" by B. Dolezel et al., in Biomaterials, 1989 Mar. vol. 10.

"Foreign-Body Giant Cells and Polyurethane Biostability: In Vivo Correlation of Cell Adhesion and Surface Cracking", by Q. Zhao, in Journal of Biomedical Materials Research, vol. 25, 177–183 (1991).

*Primary Examiner*—David Isabella
*Attorney, Agent, or Firm*—Daniel W. Latham; Harold R. Patton

[57] ABSTRACT

The present invention provides resistance to degradation from environmental stress cracking (ESC) and metal ion induced oxidation (MIO) for implantable, flexible pacing lead insulators having a body of polyether polyurethane elastomer material. A thin layer of a second polyurethane elastomer is applied as an overcoat to the lead insulator body. The second polyurethane is more resistant to ESC and MIO than the elastomer comprising the body of the insulator. Because ESC and MIO are surface phenomina, only a thin layer of the second material is required and the mechanical properties of the base material will determine the overall mechanical properties of the lead insulator.

4 Claims, No Drawings

PACING LEAD INSULATOR

This is a continuation-in-part of U.S Ser. No. 07/825,694 filed Jan. 27, 1992, now abandoned.

BACKGROUND OF THE INVENTION

This invention relates to implantable prostheses and to methods for making them less susceptible to degradation when inplanted in vivo for extended periods of time. In particular, it concerns elastomeric polyurethane insulators for implantable electrical leads such as those used in cardiac pacing.

Background on biostability of implantable polyurethane elastomers and devices such as pacing leads can be found in Coury et al., "Biostability Considerations for Implantable Polyurethanes" Life Support Systems, (1987) 5, 25–39 and in Stokes, "The Biostability of Polyurethane Leads" Modern Cardiac Pacing, Barold S. Serge, Ed., Mount Kisco, N.Y.: Futura Pub. Co, 1985, pp. 173-98. In general, it is acknowledged that there are a number of mechanisms for degradation of elastomeric polyurethane pacing leads in vivo. One is environmental stress cracking (ESC), the generation of crazes or cracks in the polyurethane elastomer produced by the combined interaction of a medium capable of acting on the elastomer and a stress level above a specific threshold. Another is metal ion induced oxidation (MIO) in which polyether urethane elastomers exhibit accelerated degradation from metal ions such as cobalt ions, chromium ions, molybdenium ions and the like which are used alone or in alloys in pacing lead conductors.

It is believed that the ether linkages in the polyether urethane elastomers are susceptible to in vivo attack by these mechanisms. Unfortunately, the most desirable polyether urethane elastomers for pacing lead insulators are the most flexible polyurethanes which contain the most ether groups which are subject to ESC and MIO attack. For example, PELLETHANE 2363-80A is regarded as having nearly ideal flexural properties for pacing lead designs while PELLETHANE 2363-55D is regarded as being too stiff for many pacing lead designs. It is well known, however, that the 55D material (and other harder polyether urethane elastomers) has fewer ether linkages than the 80A material and is therefore superior in resistance to the identified mechanisms of in vivo degradation. Efforts have also been made to develop polyurethane elastomers for pacing lead insulators which have essentially no ether linkages such as those disclosed in U.S. Pat. No. 4,875,308 to Coury et al.; International Patent Application WO 92/04390; U.S. Pat. No. 5,133,742 to Pinchuk; and U.S. Pat. No. 5,109,077 to Wick. However, it is not yet clear whether any of these efforts to make a substantially ether-free polyurethane elastomer will provide a biostable polyurethane elastomer with mechanical properties as desirable as the mechanical properties of the PELLETHANE 80A now favored for use in polyurethane lead insulators.

U.S. Pat. No. 4,851,009 issued to Pinchuk employs a silicone rubber, typically a siloxane as a barrier coating over polyurethane to prevent in vivo cracking of the polyurethane. Unfortunately, the application of the silicone may require extensive treatments including the use of coupling agents, primer coats, exposure to a free radical initiator and the like. In addition, placing silicone over the polyurethane deprives the pacing lead some of the main advantages of polyurethane; the low coeficient of friction of polyurethane when wet that makes polyurethane leads easier to insert and maneuver when two or more leads are inserted in one vein and the toughness of polyurethane in resisting surface mechanical damage.

Additional background on the problem with polyurethanes can be found in Zhao et al., "Foreign-body giant cells and polyurethane biostability: In vivo correlation of cell adhesion and surface cracking", J. Biomedical Materials Research, Vol. 25, 177–183 (1991); and Zhao et al., "Cellular interactions with biomaterials: in vivo cracking of pre-stressed PELLETHANE 2363-80A", J. Biomedical Materials Research, Vol. 24, 621–627 (1990). Dolezel et al in "In vivo degradation of polymers" Biomaterials 1989, Vol. 10, 96–100, describes problems with polyethylene and silicone rubber in vivo.

It is therefore an object of the present invention to provide a polyurethane pacing lead insulator with improved resistance to in vivo degradation.

It is also an object of the present invention to provide a pacing lead insulator having excellent flexibility and mechanical properties.

SUMMARY OF THE INVENTION

These and other objects have been accomplished by the present invention. We have discovered that where a flexible pacing lead insulator has a body of a polyurethane elastomer which is susceptible to degradation cracking when implanted in vivo over substantial time periods due to a high concentration of ether linkages, a thin layer of a second polyurethane elastomer can be applied with a second, lower concentration of ether linkages to provide a lead insulator with resistance to ESC and MIO while maintaining the flexibility of the base elastomer. The second elastomer is selected from the group consisting of a polyether urethane elastomer having a hardness at least about 90A on the Shore A scale and a substantially ether-free biostable polyurethane elastomer.

The overlayer may be applied by dip coating, spraying or co-extrusion to provide a favorable combination of the properties of the two different materials. The bulk of the insulator material would be a soft polyurethane having the desired flexibility, preferably a polyether urethane elastomer having a hardness of 80A on the Shore A scale. Since ESC and MIO are surface phenomena, a thin layer of the second polyurethane overlayer (e.g. about 5 microns to about 0.002 inches (0.005 cm) thick) provides favorable resistance to these degradation mechanisms without appreciably changing the overall flexibility the lead insulator. Therefore, even if the mechanical properties of the ESC and MIO resistant polyurethane are suboptimal for use in pacing lead insulators alone, they can be used in combination with a material that will provide the desired mechanical properties. Also, since the materials employed for the base material and the overlayer are both polyurethanes, they have similar chemical and physical properties so that the thin layer of the second elastomer can be applied without the need for cumbersome and expensive surface treatments to the base material. The lamination may overlay the base polyurethane on the outside of the lead insulator to prevent ESC, the inner lumen of the lead insulator to prevent MIO or both.

DETAILED DESCRIPTION OF THE INVENTION

The present invention provides a base insulation of soft polyurethane elastomer overcoated with a thin layer of a polyurethane elastomer with a relatively low concentration of ether linkages such as an aliphatic or aromatic polyether urethane having a hardness at least about 90A on the Shore A scale or a biostable ether-free polyurethane elastomer. Since the environmental stress cracking (ESC) in such implantable devices is a surface phenomenon, very little of the second elastomer needs to overlay the softer layer. A thin layer, on the order of 0.001 inches (0.0254 mm), of the is all that is required to impart superior ESC and MIO resistance to implantable devices. Such thicknesses do not appreciably change the overall handling characteristics of the completed device, while increasing the ESC resistance.

METHODS OF APPLICATION

The lamination of the second material layer may be accomplished using any of the existing well known methods including dipping, spraying, and co-extrusion, with co-extrusion being preferred. The layer of second material should generally be in the range of about 0.001 inches (0.0254 mm) in thickness, although it may be thinner or thicker depending on the application needs.

Coating of polymeric biomedical devices by dipping, spraying, or co-extrusion techniques are known to those skilled in the art. Special care and understanding of polymer biostability are required to provide the optimum product performance. For example, care must be exercised to minimize antioxidant removal (by thermal or extractive means), to minimize residual stress in the parts, and to engineer consistent reliable processes.

ACCEPTABLE OVERLAYING MATERIALS

The acceptable second, overlaying material will be a polyurethane elastomer; either a polyether urethane elastomer having a hardness on the Shore A durometer scale of at least about 90A or a substantially ether-free polyurethane elastomer. The elastomer must also be oxidatively and hydrolytically stable and have a toughness in the range of polyurethanes generally. A suitable urethane is PELLETHANE 2363-55D or PELLETHANE 2363-55DE of Dow Chemical Co. of Midland, Mich. Polyurethanes essentially equivalent to PELLETHANE 2363-55D are available from other sources such as B. F. Goodrich, Inc. The PELLETHANE 2363 family of polymers, including 2363-80A and 2363-55D, are composed of methylene bis isocyanato benzene (MDI), butane diol (BD) hard segments and polytetramethylene ether oxide (PTMO) soft segments. The proportion of hard to soft segments is higher for the harder (Shore 55D) polymer than for the softer (Shore 80A) material thereby providing fewer ether linkages which may be subject to in vivo degradation.

Preferably, the urethane is a substantially ether-free polyurethane since stress cracking appears to have a relation to the ether content of the polymer, with fewer ether linkages being desirable. A polymer without ether linkages may be made by substituting aliphatic, polycarbonate or polydimethylsiloxane groups for the polyether groups of the soft segments. Ether-free polyurethanes said to be suitable for in vivo use are disclosed in U.S. Pat. No. 4,875,308 to Coury et al.; published International Patent Application WO 92/04390; U.S. Pat. No. 5,133,742 to Pinchuk; and U.S. Pat. No. 5,109,077 to Wick which are incorporated herein by reference in their entirety. Biostable ether-free polymers include PolyMedica's Chronoflex AL-80A and Chronoflex AL-55D; Medtronic, Inc.'s family of biostable polyurethanes (U.S. Pat. No. 4,873,308) and AKZO/ENKA'S PUR series of polyurethanes. These materials are coatable over the preferred lead insulator material, PELLETHANE 2363-80A, by methods such as solution coating or coextrusion.

IMPLANTABLE DEVICES

The ESC and MIO reduction of the invention may be achieved with many implantable medical devices. Such medical devices can include insulator sheaths of cardiac pacemaker leads, artificial heart diaphragms, artificial heart valve leaflets, sewing cuffs and the like. However, the preferred use of the invention is to provide improved resistance to degradation in critical lead insulation applications. In a typical lead and lead insulator assembly, an elastomeric polyurethane insulator is the outer element through which coiled conductors pass. The configuration can include separate, mutually insulated coils in which the multiple coils are carried in separate insulator passages in coaxial or side-by side arrangement or multi-polar coiled conductors having individually insulated coil wires which pass through an outer insulator sheath of polyurethane elastomer. Such a lead system is disclosed in greater detail in U.S. Pat. No. 5,040,544 issued to Lessar et al. which is incorporated herein by reference in its entirety. In such lead systems, the polyurethane lead insulator is essentially an extruded piece of tubing of the desired shape and size required to carry the conductors. An outside diameter of the insulator is typically in the range of about 0.020" to 0.090" with a wall thickness typically in the range of about 0.005" to 0.010". In the following examples, implanted tubing samples such as those used for pacing lead insulators were provided with materials and treatments intended to address the issues of ESC and MIO.

The effect of using an overlaying material of differing mechanical properties can be easily calculated for a pacing lead insulator. For a composite tube having an inner, base material and an overlaying, outer material, the following formula can be applied to determine its stiffness:

$$(EI)_{COMPOSITE} = \pi \frac{E_1}{64}(d_2^4 - d_1^4) + \pi \frac{E_2}{64}(d_3^4 - d_2^4)$$

Where $E_1$ is the elastic modulus of the base material, $E_2$ is the elastic modulus of the overlaying material, $d_1$ is the inside diameter of the base material, $d_2$ is the outside diameter of the base material and the inside diameter of the overlaying material, and $d_3$ is the outside diameter of the overlaying material. Therefore, if one wished to provide a pacing lead insulator with a base material of PELLETHANE 80A and with an overlaying layer of PELLETHANE 55D, the relative overall stiffness of the lead insulator would be as set forth in Table 1.

TABLE 1

STIFFNESS OF CO-EXTRUDED PACING LEAD INSULATION

| COATING THICKNESS (in) | ELASTIC MODULUS $E_1$ | ELASTIC MODULUS $E_2$ | INSIDE DIAMETER $d_1$ (in) | BASE OUTSIDE DIAMETER $d_2$ (in) | COATING OUTSIDE DIAMETER $d_3$ (in) | STIFFNESS (EI) COMPOSITE |
|---|---|---|---|---|---|---|
| All P80 A | 3,400 | — | 0.073 | 0.093 | — | 7.7 |
| 0.0005 | 3,400 | 10,200 | 0.073 | 0.0925 | 0.093 | 8.3 |
| 0.001 | 3,400 | 10,200 | 0.073 | 0.092 | 0.093 | 8.8 |
| 0.0015 | 3,400 | 10,200 | 0.073 | 0.0915 | 0.093 | 9.3 |
| 0.002 | 3,400 | 10,200 | 0.073 | 0.091 | 0.093 | 9.9 |
| All P55D | — | 10,200 | 0.073 | 0.093 | — | 23 |

It is therefore apparent that a co-extruded coating with a stiffer material causes little change in the stiffness of the lead insulator. A lead insulator of PELLETHANE 55D would be roughly three times as stiff as a lead insulator of PELLETHANE 80A and yet a coextruded lead insulator with a 0.001 inch coating of PELLETHANE 55D over a base of PELLETHANE 80A can be expected to have a stiffness only about 14% greater than the stiffness of the insulator made with PELLETHANE 80A alone.

EXAMPLE 1

Five different tubings were fabricated and implanted in rabbits to study ESC resistance. The tubings had a 0.073 inch (0.185cm) ID (inside diameter) by a 0.093 inch (0.236 cm) OD (outside diameter). The test material strands consisted of five polysulfone dumbbell shaped mandrels (each approximately 0.165 cm diameter by 1.27 cm long). Each dumbbell supported a sample of strained (400%) or unstrained (0%) test or control tubing. 2-0 Ticron suture was used to sustain the strain of these samples. Five individual samples were tied together to form a strand. Each strand was identified with an attached colored glass bead. There was a total of 130 samples, with 10 samples for each condition explanted at 12 weeks.

Tubing samples were formed by co-extruding either PELLETHANE 2363-55D (P55D) tubing or PELLETHANE 2363-55DE (P55DE) over PELLETHANE 2363-80A (P80A). The test tubings were then compared to the ESC resistance of positive and negative control samples, respectively, P80A tubing and P55D tubing. Control tubing conditions and test tubing conditions are given below.

CONTROL TUBING CONDITIONS

A PELLETHANE 2363-80A, PN153097-050, Lot #448907: 0% elongation, annealed PELLETHANE 2363-80A, PN153097-050, Lot #448907: 400% elongation, annealed B PELLETHANE 2363-55D, PN153097-064, Mier 39513, 0% elongation PELLETHANE 2363-55D, PN153097-064, Mier 39513, 400% elongation

TEST TUBING CONDITIONS

C P80A/P55DE, wall thickness 0.0045 inches (0.011 cm)/0.002 inches (0.005 cm). 0% elongation. P80A/P55DE, wall thickness 0.0045 inches (0.011 cm)/0.002 inches (0.005 cm). 400% elongation.

D P80A/P55D, wall thickness 0.0045 inches (0.011 cm)/0.002 inches (0.005 cm). 0% elongation. P80A/P55D, wall thickness 0.0045 inches (0.011 cm)/0.002 inches (0.005 cm). 400% elongation.

E P80A/P55D, wall thickness 0.007 inches (0.018 cm)/ 0.001 inches (0.003 cm). 0% elongation. P80A/P55D, wall thickness 0.007 inches (0.018 cm)/ 0.001 inches (0.003 cm). 400% elongation.

SAMPLE ANALYSIS

The test material strands were implanted subcutaneously in rabbits and removed at 12 weeks. The samples were examined at 30× to 70× magnification for ESC and defects. The samples were then rated for environmental stress cracking with results reported as a fraction, X/Y. The definitions of X and Y are:

X=Depth of cracks
0=No change in the surface
1=A change in the surface but no cracks at 70X
2=Very shallow cracks at 70X
3=Cracks up to half way through the tubing wall
4=Cracks greater than 50% of the tubing wall but not to 100%
5=Cracks 100% through the tubing wall
Y=Surface area affected
0=No change in the surface
1=$\leq 20\%$
2=>20%, $\leq 40\%$
3=>40%, $\leq 60\%$
4=>60%, $\leq 80\%$
5=>80% of surface The results of the study are tabulated in Table 2.

TABLE 2

ESC Resistance of Co-Extruded Tubing P80A/P55D and P80A/P55IDE at 12 weeks

| Rabbit # | % Strain | Condition A | Condition B | Condition C | Condition D | Condition E |
|---|---|---|---|---|---|---|
| 311 | 0% | 1/1 | 0/0 | 0/0 | 0/0 | 0/0 |
|  | 0% | 1/3 | 0/0 | 0/0 | 0/0 | 0/0 |
|  | 400% | 1/3 | 0/0 | 0/0 | 0/0 | 0/0 |
|  | 400% | 1/3 | 0/0 | 0/0 | 0/0 | 0/0 |
| 318 | 0% | 1/2 | 0/0 | 0/0 | 0/0 | 0/0 |
|  | 0% | 1/2 | 0/0 | 0/0 | 0/0 | 0/0 |
|  | 400% | 2/1 | 0/0 | 0/0 | 0/0 | 0/0 |
|  | 400% | 1/2 | 0/0 | 0/0 | 0/0 | 0/0 |
| 320 | 0% | 0/0 | 0/0 | 0/0 | 0/0 | 0/0 |
|  | 0% | 1/2 | 0/0 | 0/0 | 0/0 | 0/0 |
|  | 400% | 2/1 | 0/0 | 0/0 | 0/0 | 0/0 |
|  | 400% | 1/2 | 0/0 | 0/0 | 0/0 | 0/0 |
| 321 | 0% | 0/0 | 0/0 | 0/0 | 0/0 | 0/0 |

TABLE 2-continued

| | | ESC Resistance of Co-Extruded Tubing P80A/P55D and P80A/P55IDE at 12 weeks | | | | |
|---|---|---|---|---|---|---|
| Rabbit # | % Strain | Condition A | Condition B | Condition C | Condition D | Condition E |
| | 0% | 0/0 | 0/0 | 0/0 | 0/0 | 0/0 |
| | 400% | 2/1 | 0/0 | 0/0 | 0/0 | 0/0 |
| | 400% | 0/0 | 0/0 | 0/0 | 0/0 | 0/0 |
| 325 | 0% | 0/0 | 0/0 | 0/0 | 0/0 | 0/0 |
| | 0% | 0/0 | 0/0 | 0/0 | 0/0 | 0/0 |
| | 400% | 1/2 | 0/0 | 0/0 | 0/0 | 0/0 |
| | 400% | 0/0 | 0/0 | 0/0 | 0/0 | 0/0 |

Conditions:
A = P80A Controls, stress relieved
B = P55D Controls
C = P80A/P55DE
D = P80A/P55D
E = P80A/P55D No ESC was observed on any of the co-extruded tubing samples. No ESC was found on the PELLETHANE 55D control (negative) samples, whereas four PELLETHANE 80A control (positive) samples had areas of shallow ESC.

EXAMPLE 2

PELLETHANE 2363-80A tubing was coated with a solution of Enka polyurethane PUR 981, Medtronic biostable polyurethane, and alternatively, PELLETHANE 2363-55D. A 12% stock solution of the coating polymer in DMAC was cut to a 2% solution and used to dip coat cut segments of PELLETHANE 80A tubing. A 2% solution of PELLETHANE 80A containing Blue Dextran in DMAC and a 2% solution of MDX silicone in hexane were also used to dip coat cut segments of PELLETHANE 80A tubing. The P80A tubing segments were cleaned in isopropyl alcohol and then dipped and withdrawn smoothly from a cylinder containing the overcoat polymer. The dipped tubing was allowed to drip several seconds and then hung in a 40° C. forced air oven with the circulation off. After 10 to 20 minutes the air and heat were turned on for at least one hour between each coat. A total of 4 coats was applied. Finally, the coated tubes were dried overnight at 40° C. in the oven with heat and air circulation on. The MDX tubing samples were dried for an additional 2 days.

PELLETHANE 80A tubing segments were also surface-grafted with an acrylamide solution. Clean P80A tubing segments were placed into a 40% acrylamide in DI water solution containing ceric ion for 25 minutes. The ceric ion causes the graft copolymerization of acrylamide on the surface of the tubing. Following surface-grafting the samples were rinsed thoroughly in DI water.

Segments of PELLETHANE 80A/55DE coextruded tubing and PELLETHANE 80A tubing were also tested in this study for ESC resistance. The tubing specimens in this study were tested and analyzed for ESC according to the procedures described in Example 1, the results of which are set forth in Table 3 shown below.

TABLE 3

| | Biostability Study of Surface Treatments on Pellethane 2363-80A Tubing Strained 400% | | | | | | | |
|---|---|---|---|---|---|---|---|---|
| Rabbit # | Conditions A | B | C | D | E | F | G | H |
| 104 | 0/0 | 0/0 | 0/0 | 1/2 | 0/0 | 0/0 | 0/0 | 0/0 |
| | 0/0 | 0/0 | 0/0 | 2/3 | 0/0 | 0/0 | 0/0 | 0/0 |
| 105 | 5/1 | 5/3 | 5/4 | 5/4 | 5/1 | 0/0 | 0/0 | 2/2 |
| | 0/0 | 0/0 | 0/0 | 4/1 | 5/1 | 0/0 | 0/0 | 5/1 |
| 107 | 5/1 | 5/2 | 5/2 | 5/3 | 0/0 | 0/0 | 0/0 | 0/0 |
| | 1/1 | 2/2 | 5/1 | 5/4 | 5/1 | 0/0 | 0/0 | 5/2 |
| 108 | 5/1 | 5/1 | 4/2 | 5/3 | 0/0 | 0/0 | 0/0 | 1/2 |
| | 0/0 | 0/0 | 0/0 | 1/2 | 5/1 | 0/0 | 0/0 | 1/3 |
| 109 | 1/2 | 5/1 | 5/1 | 5/1 | 0/0 | 0/0 | 0/0 | 5/3 |
| | 0/0 | 4/1 | 5/4 | 5/4 | 5/1 | 0/0 | 0/0 | 4/1 |
| 110 | 0/0 | 5/2 | 5/1 | 5/3 | 5/1 | 0/0 | 0/0 | 0/0 |
| | 0/0 | 0/0 | 0/0 | 0/0 | 5/1 | 0/0 | 0/0 | 1/5 |

Conditions:
A. Enka
B. Biostable
C. MDX Silicone
D. Acrylamide grafted
E. Blue dextran/P80A
F. P55D
G. P55DE coextruded P80A
H. Pellethane 2363-80A (control)

No ESC was observed on the P55D dip coated and P55DE coextruded samples. All other tubing specimens had varying amounts of ESC.

This completes the description of the preferred and alternate embodiments of the invention. Those skilled in the art may recognize other equivalents to the specific embodiment described herein which equivalents are intended to be encompassed by the claims attached hereto.

While this invention may be embodied in many different forms, described in detail herein specific preferred embodiments of the invention. The present disclosure is an exemplification of the principles of the invention and is not intended to limit the invention to the particular embodiments illustrated.

What is claimed is:

1. In a flexible pacing lead insulator which has a body of a first polyurethane elastomer which is susceptible to degradation cracking when implanted in vivo over substantial time periods, said elastomer having a first concentration of ether linkages, the improvement comprising a thin layer of a second polyurethane elastomer on said body, said second elastomer having a second, lower concentration of ether linkages, said second elastomer selected from the group consisting of a polyether urethane elastomer having a hardness at least about 90A on the Shore A scale and a substantially ether-free biostable polyurethane elastomer.

2. The lead insulator of claim 1 wherein the first polyurethane elastomer has a Shore durometer hardness of about 80A.

3. The lead insulator of claim 1 wherein the second polyurethane elastomer has a Shore durometer hardness of about 55D.

4. The lead insulator of claim 1 wherein the layer of the second polyurethane elastomer has a thickness in the range of about 5 microns to about 0.002 inches.

* * * * *